(12) United States Patent
Pechstein et al.

(10) Patent No.: US 7,394,263 B2
(45) Date of Patent: Jul. 1, 2008

(54) SENSOR ARRANGEMENT WITH A PLURALITY OF POTENTIOMETRIC SENSORS

(75) Inventors: Torsten Pechstein, Radebeul (DE); Wolfgang Babel, Weil der Stadt (DE); Thomas Steckenreiter, Frankfurt (DE)

(73) Assignee: Endress + Hauser Conducta Gesellschaft fur Mess-u. Regeltechnik mbH +Co. KG, Gerlingen (DE)

( * ) Notice: Subject to any disclaimer, the term of this patent is extended or adjusted under 35 U.S.C. 154(b) by 0 days.

(21) Appl. No.: 10/578,865

(22) PCT Filed: Oct. 28, 2004

(86) PCT No.: PCT/EP2004/012182

§ 371 (c)(1),
(2), (4) Date: Apr. 2, 2007

(87) PCT Pub. No.: WO2005/047878

PCT Pub. Date: May 26, 2005

(65) Prior Publication Data

US 2007/0273395 A1    Nov. 29, 2007

(30) Foreign Application Priority Data

Nov. 11, 2003   (DE) ................. 103 52 917

(51) Int. Cl.
*G01R 27/00* (2006.01)

(52) U.S. Cl. ............ 324/714; 324/71.1; 324/450; 324/438; 204/433; 435/4

(58) Field of Classification Search ......... 234/714, 234/71.1, 438, 439, 443, 444, 450; 435/4; 204/433; 324/714, 71.1, 438, 439, 443, 444, 324/450

See application file for complete search history.

(56) References Cited

U.S. PATENT DOCUMENTS

2002/0152037 A1 * 10/2002 Sunshine et al. ............. 702/23

(Continued)

FOREIGN PATENT DOCUMENTS

DE      198 57 953  A1    7/2000

(Continued)

OTHER PUBLICATIONS

I-Yu Huang et al., "Improvement of Integrated Ag/AgCl Thin-Film Electrodes by KCl-Gel Coating for ISFET Applications", 2003, Elsevier Science B.V.

(Continued)

*Primary Examiner*—Vincent Q Nguyen
(74) *Attorney, Agent, or Firm*—Bacon & Thomas, PLLC

(57) ABSTRACT

The sensor arrangement includes: a least two sample chambers; at least two potentiometric FET-sensors, especially ISFET-sensors or ChemFET-sensors, having, in each case, a sensitive surface section, wherein each sensitive surface section lies in flow connection with its one of the sample chambers; and a reference cell having a reference medium for providing a reference potential, wherein the sample chambers are connected with the reference medium via an electrolyte bridge. The reference cell has, preferably, a potentiometric reference-FET-sensor for providing a reference potential, which is registered against the pseudo-reference-potential of a redox electrode. The potentials $U_{diff1}$, $U_{diff2}$, ... $U_{diffN}$ of N FET-sensors in the sample chambers are determined against the pseudo-reference-potential, and the measured-variable-relevant, potential differences are determined, in each case, by difference formation between the pertinent potential and the reference potential—thus, in the case of pH, according to the formulas $$U_{pH1}...N = U_{diff1}...N - U_{diffref}$$

13 Claims, 2 Drawing Sheets

U.S. PATENT DOCUMENTS

2006/0073539 A1* 4/2006 Wikswo et al. .............. 435/29

FOREIGN PATENT DOCUMENTS

| EP | 5 905 2745 | 3/1984 |
| EP | 1 460 130 A1 | 9/2004 |
| WO | WO 94/06005 | 3/1994 |
| WO | WO 03/052097 A1 | 6/2003 |

OTHER PUBLICATIONS

A. Poghossian et al., "Application of a (bio-)chemical sensor (ISFET) for the detection of physical parameters in liquids", 2003, Elsevier Science Ltd.

C. Cane et al., "Microtechnologies for pH ISFET chemical sensors", 1997 Elsevier Science Limited.

T.C. W. Yeow et al., "A very large integrated pH-ISFET sensor array chip compatible with standard CMOS Processes", 1997, Elsevier Science, S.A.

H. Suzuki et al., "Micromachined liquid-junction Ag/AgCl reference electrode", 1998, Elsevier Science S.A.

P. Bergveld, "Thirty Years of ISFETOLOGY What happened in the past 30 years and what may happen in the next 30 years", 2002 Elsevier Science B.V.

* cited by examiner

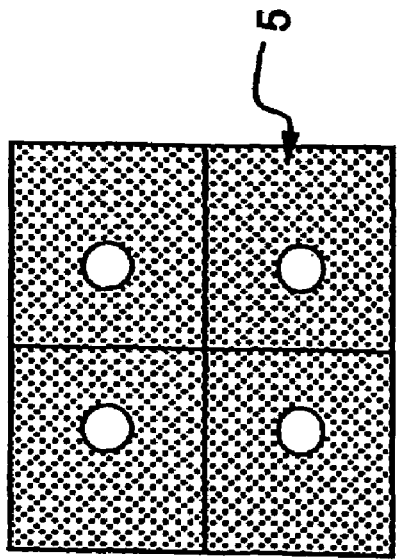
Fig. 2b
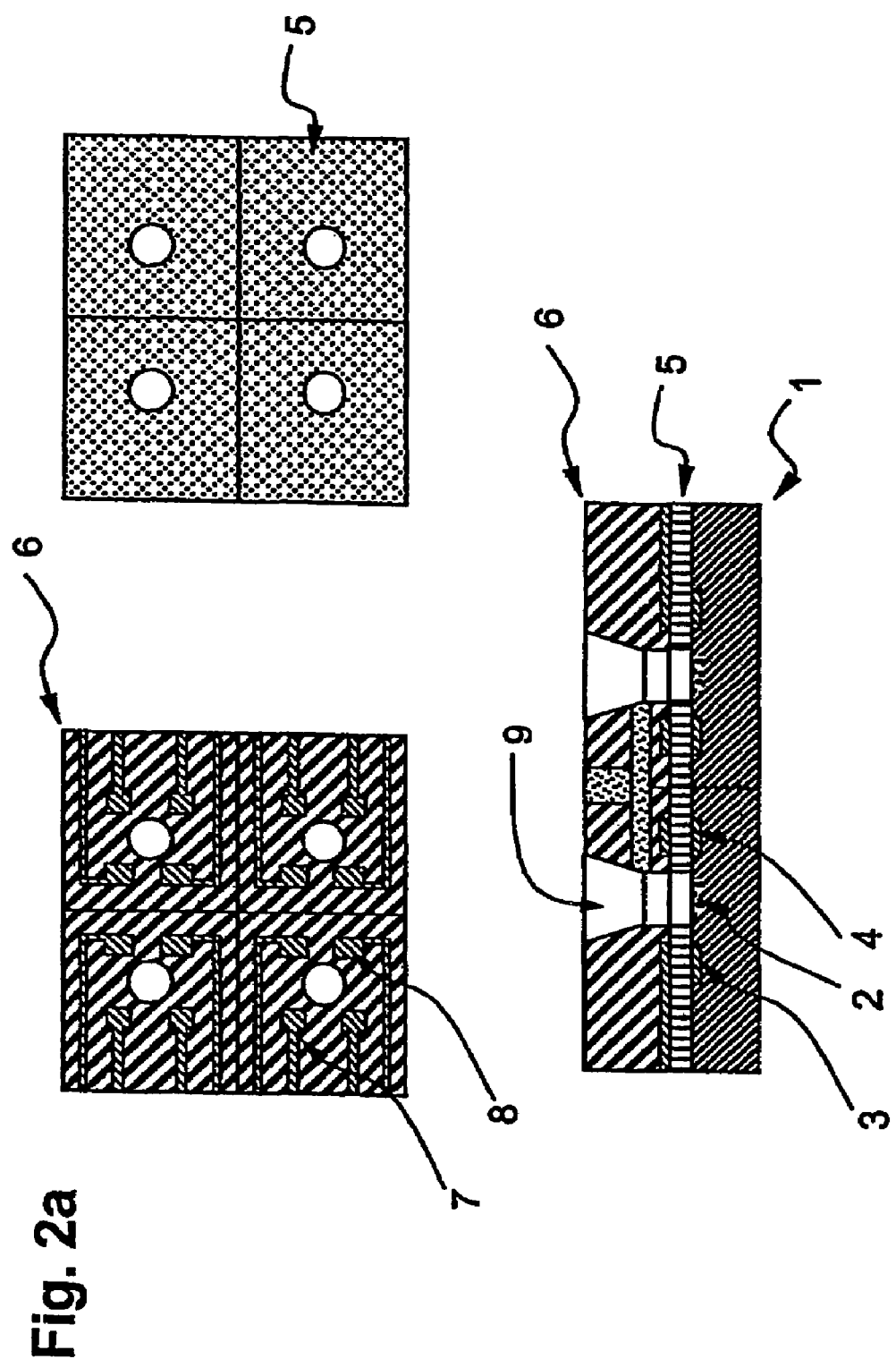
Fig. 2a
Fig. 2c

US 7,394,263 B2

SENSOR ARRANGEMENT WITH A PLURALITY OF POTENTIOMETRIC SENSORS

FIELD OF THE INVENTION

The present invention relates to a sensor arrangement for the potentiometric testing of a plurality of samples, especially such an arrangement having so-called ISFET or CHEMFET sensors.

BACKGROUND OF THE INVENTION

These kinds of potentiometric FET-sensors are suited for measuring the pH value or the redox potential of an analyte. DE 198 57 953 C2 concerns, for example, the realization of a pH-ISFET-sensor, in which, for reducing the circuit complexity, the ISFET-sensor is connected in a bridge circuit having at least three additional resistances. Regarding the mounting of the FET-sensor, the following principles are, among others, known. Benton discloses in U.S. Pat. No. 5,833,824 a pH-sensor, in which an ISFET-chip is secured on the underside of a substrate by means of a metal seal, which surrounds the ion-sensitive region of the ISFET-chip, with the ion-sensitive region being aligned with an opening in the substrate. Outside of the region surrounded by the seal, conductive traces on the surface of the chip are directed to contact areas, which are connected via solder, braze or weld connections with complementary contact areas on the underside of the substrate. The solution proposed by Benton is very complex, to the extent that, both in the case of the manufacture of the seal and also in the case of the implementation of the electrical contacting, involved solder, braze, or weld processes are required. $The state of the art discussed in Benton describes ISFET-sensors, in which an ordinary polymer seal is arranged about the opening of the sample chamber wall between the substrate and the ion-sensitive region of the ISFET-chip. The contacting of the ISFET-chip occurs, however, not to the substrate in the sense of Benton, but, instead, to a carrier, which supports the ISFET-chip on the rear side facing away from the substrate. For this purpose, bond wires are led between contact areas on the front side of the ISFET-chip to contact areas on the carrier outside of the bearing surface of the ISFET-chip. Also, this solution is complicated, because bonding tasks are required for contacting the chip, and because, for assuring function and integrity of the sensor, the chip must be oriented within narrow tolerances, both with reference to the substrate and with reference to the carrier. $Additionally, solutions are known, in which the chips have their contact areas, or bonding pads, on the rear side facing away from the ion-sensitive region. These chips can then be contacted on the rear side via a carrier having complementary contact areas, with an anisotropic, elastic conductor, e.g. a silicone foil with embedded gold threads, being arranged in a direction perpendicular to the plane of the foil, for assuring adequate galvanic contact between the rear side of the chip and the carrier. These solutions are very expensive hi-the with respect that to the leading of the electrical contacts through the chip from its front side to its rear side1 makes making its manufacturing costs a number of times greater.

In the unpublished German Patent Application No. 10260961.6 of the assignee of the present application, a sensor arrangement is disclosed having a single ISFET-, or CHEMFET-, sensor with a front-side mounting by means of an anisotropic conductor.

SUMMARY OF THE INVENTION

The described sensor arrangements are made only for the testing of single samples. It is, therefore, an object of the present invention to provide a sensor arrangement for potentiometric measurements, wherein, on the one hand, minimal sample volumes can be measured and, on the other hand, a plurality of samples can be simultaneously tested.

The object is achieved according to the invention by the sensor arrangement of the invention which includes: At least two sample chambers; at least two potentiometric FET-sensors, especially ISFET-sensors or ChemFET-sensors, each possessing a sensitive surface section, with each sensitive surface section being in flow-connection with a respective one of the sample chambers; a reference cell having a reference medium for providing a reference potential, and with the sample chambers being connected with the reference medium via an electrolyte bridge.

The sensor arrangement is modularly structured in an embodiment of the invention, i.e. the sample chambers are arranged in a first module and the potentiometric FET-sensors are in a second module.

The first module can include, for example, a plate-shaped platform, which contains the bores serving as the sample chambers. In the case of bores going all the way through, the potentiometric FET-sensors can be integrated into a second module, which, as a floor-element, closes the bores from the underside of the platform. For each sample chamber, a separate floor element can be provided, or a plurality of sample chambers can be closed by one floor element.

An electrolyte bridge can be effected via electrolyte canals. In a currently preferred example of an embodiment, the platform contains the electrolyte canals. The platform can be one piece or it can be composed of a plurality of elements, or a plurality of layers. In the latter case, it is advantageous to have the electrolyte canals be arranged in the interface between two layers.

In a further embodiment, the electrolyte canals are integrated into the second module, especially into the floor element.

The reference cell can likewise include a potentiometric FET-sensor for providing a reference potential, with the reference potential $U_{diffref}$ being measured against the pseudo-reference-potential of a redox electrode. The redox electrode communicates likewise with the reference medium in the reference cell. The redox electrode can comprise, for example, a metal contact with a silver, or silver-chloride, coating.

The potentials $U_{diff1}$, $U_{diff2}$, ... $U_{diffN}$ of the N FET-sensors in the sample chambers are preferably measured against the pseudo-reference potential. The measured-variable-relevant, potential difference, for example $U_{pH1}$, is determined by forming the difference between the pertinent potential and the reference potential, e.g. $U_{pH1}=U_{diff1}-U_{diffref}$. The difference formation can occur in analog fashion or digitally.

The FET-sensors, which can be present, for example, as separate chips or as a plurality of sensor elements in an, as required, monolithic floor element, have, in order to implement a sensor, to be arranged in such a manner that they, on the one hand, can be contacted by the possibly corrosive samples, without that, on the other hand, corrosion-sensitive components, e.g. conductive traces, come in contact with the media. To this end, an embodiment of the invention provides that FET-sensors are arranged in such a manner that the ion-sensitive surface regions of the FET-sensors align with bores of the sample chambers, with a ring-shaped seal being arranged between the platform and the FET-sensors. The seal surrounds the bores, so that the ion-sensitive region of the semiconductor chip can be contacted by the sample, without the sample coming in contact with the FET-sensor outside of the region enclosed by the seal. For the electrical contacting of the FET-sensors, various embodiments are possible.

Currently, the principle of construction of the German Patent Application No. 10260961.6 already mentioned above is preferred. According to this, the FET-sensors have on the first contact areas facing toward the platform first contact areas, which align with fitting, second contact areas on the underside of the platform facing toward the FET-sensor. The underside of the platform has conductive traces, via which the second contact areas are electrically connected with suitable circuits for supplying the FET-sensors. Between the underside of the platform and the upper surface of the FET-sensor, an elastic layer, or foil, is arranged, which is, at least sectionally, anisotropically conductive perpendicular to the upper surface of the FET-sensor, with the elastic layer having an opening, which is aligned with the bore. The elastic foil, or layer, serves, thus, on the one hand, as a seal and, on the other hand, for electrical contacting.

Preferably, the elastic, insulating layer or foil includes conductive particles, grains or threads, especially metal particles or threads, embedded in the anisotropically conductive region. Especially preferred at this time are gold threads, which extend perpendicularly to the plane of the elastic, organic layer. Especially preferred at this time are silicone layers, which contain gold threads and which are commercially available from the firm, Shin-Etsu.

To the extent that the elastic layer contains metal grains, these are uniformly distributed in the case of a relaxed layer in such a concentration that there is not a sufficient number of electrical contacts between the grains to produce an electrical conductivity over large distances. If, however, the elastic layer is compressed in some direction, for example by being clamped as a sealing element between the first module and the second module, or between the platform and the floor element, as the case may be, then there arises in the direction of compression a sufficient number of electrical contacts for assuring conductivity along the direction of compression. Independently of the selected type of sealing element, the FET-sensors, or the floor element, can be pressed by a rear-side support against the elastic layer, in order to optimize the sealing effect of the elastic layer. The rear-side support can be both stiff as well as also elastically prestressed. The elastic prestressing, e.g. with a coil spring, is advantageous in the respect that, thereby, the effects of different coefficients of thermal expansion can be safely accommodated, as compared with accomplishing such solely by the elasticity of the sealing element. This is especially important, when a certain degree of compression of the sealing element is required, in order to assure the electrical conductivity through the seal.

The other known types of contacting of the FET-sensor, for example according to Benton, or according to the state of the art discussed in Benton, are likewise suited for realizing the present invention, with, in the case of a contacting according to Benton, the disadvantage that has to be lived with being that a fixed connection is made between the FET-sensor and the platform, whereby the modularity is impaired.

BRIEF DESCRIPTION OF THE DRAWINGS

FIG. 2a a bottom view of a platform for a sensor arrangement according to the present invention;

FIG. 2b a sealing element for a sensor arrangement according to the present invention; and FIG. 2c a longitudinal section through a sensor arrangement according to the present invention.

DESCRIPTION OF THE PREFERRED EMBODIMENTS

Figure 1:
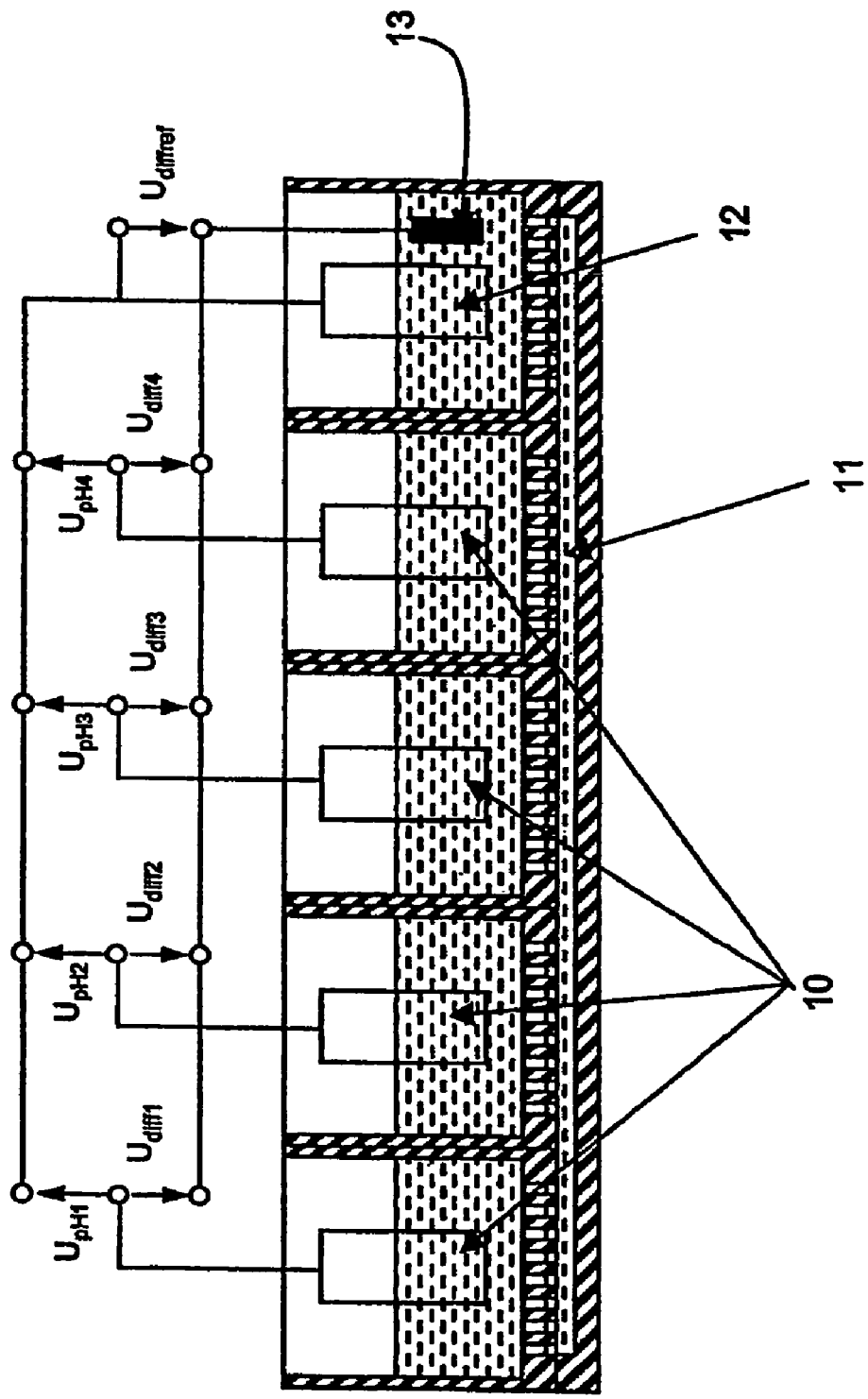
FIG. 1 a schematic drawing of the principle of functioning of a sensor arrangement according to the present invention.

FIG. 1 shows schematically the principles of functioning of the sensor arrangement of the invention. The FET-sensors 10 of the sensor arrangement have, in each case, a sensitive gate-region, which is contactable with an analyte in a sample chamber. The individual sample chambers of the sensor arrangement are connected with one anther via an electrolyte bridge. To this end, the electrolyte bridge includes an electrolyte canal, which communicates with the sample chambers via diaphragms. The sensor arrangement further includes a reference chamber, in which a reference electrode 13, for example of platinum, and reference-FET 12 are located. The reference-FET outputs a pseudo-reference-potential $U_{diffref}$, against which the potentials $U_{diff1}, U_{diff2}, \ldots U_{diffN}$ of the N FET-sensors in the sample chambers are measured. The measured-variable-relevant, potential difference, for example $U_{pH1}$, is determined by forming the difference between the applicable potential and the reference potential—thus, in the case of the example, $U_{pH1}=U_{diff1}-U_{diffref}$. The forming of the difference can be done in analog manner or digitally.

Structural details of an example of an embodiment of the sensor arrangement of the invention will now be explained on the basis of FIGS. 2a, 2b and 2c.

FIG. 2a shows the underside of a substrate 6 having four sample chambers 9 for a sensor arrangement of the invention, with, for each opening of a sample chamber, contact areas 7 and 8 being arranged spaced therefrom. The contact areas 7 and 8 are, in each case, connected via conductive traces in suitable manner with the required terminals. In the case of the sensor in its assembled state, the openings serve to enable the contacting of the sensors with the sample to be analyzed.

FIG. 2b shows a top view onto a sealing element for a sensor arrangement according to the present invention, with the sealing element, in the case of this form of embodiment comprising a silicone layer, in which traversing, gold threads have been introduced, which extend essentially perpendicularly to the plane of the sealing element 5. In this way, the sealing element is electrically insulating in the plane of the sealing element and conductive perpendicular to the plane of the sealing element. Consequently, electrical contact areas, aligned with one another but separated from one another by the seal, can be brought into electrical contact with one another, while, with reference to the plane of the sealing element, contact areas laterally displaced from one another are electrically insulated from one another.

The required minimum size of the aligned contact areas for assuring a safe contact is a matter of the average number of gold threads per unit area of the sealing element. This parameter can be adapted in suitable manner by those skilled in the art. Equally, the average lateral separation of structural elements for assuring a reliable insulation is a function of the number density of the gold threads, as well as their orientation and their diameter. At this time, a sealing element is preferred, which enables a reliable contacting in the case of aligned contact areas of even less than 1 mm$^2$ and assures a sufficient insulation in the case of a lateral separation of about 0.5 mm.

The outer dimensions of the sealing element in FIG. 2b are, in the case of this form of embodiment, congruent with the outer dimensions of the underside of the substrate in FIG. 2a; however, this is not strictly necessary. The sealing element has, additionally, openings for each sample chamber in the substrate and, as required, additionally for a reference chamber. These openings align with the corresponding openings in the substrate. It is expedient to have the openings in the sealing element exhibit about the same size as the openings in the underside of the substrate 6. In this way, dead volumes are avoided between the substrate and a semiconductor chip serving as floor element, or between the sealing element and the floor element or the substrate, as the case may be.

Then, FIG. 2c shows a longitudinal section through an assembled sensor arrangement according to the present invention, with the sealing element 5 being clamped between the semiconductor chip 1 and the substrate 6.

The semiconductor chip 1 has, in its surface facing substrate 6, ion-sensitive regions 2, which are aligned with the openings in the substrate 6. Spaced from the openings are, in each case, contact areas 3 and 4, which, in each case, align with the complementary contact areas 7, 8 on the underside of the substrate. The contacting between the chip-side contact areas 3, 4 and the substrate-side contact areas 7, 8 is assured by the conductivity of the sealing element 5 perpendicular to its plane.

In order to achieve a sufficient sealing action, the semiconductor chip must be pressed with adequate force against the underside of substrate 6. This can be done, on the one hand, by a clamping using form-stable structural elements and, on the other hand, by a prestressing by means of elastic elements. An example of an elastic element is a coil spring. Neither the clamping option nor the use of elastic elements is shown here.

The substrate 6 can be embodied as one piece with a housing of a semiconductor sensor or else provided as a separate component, which is then installed in suitable manner into a housing. These and similar variations are within the skill of the art, without departure from the fundamental concepts of the invention, as defined in the appended patent claims.

The invention claimed is:

1. A sensor arrangement, comprising:
   at least two sample chambers;
   at least two potentiometric FET-sensors, preferably ISFET-sensors or ChemFET-sensors, having, in each case, a sensitive surface section, wherein each sensitive surface section lies in flow connection with one of said at least two sample chambers; and
   a reference cell having a reference medium for providing a reference potential, wherein:
      said at least two sample chambers are connected with the reference medium via an electrolyte bridge and
      said electrolyte bridge including and electrolyte canal which communicates with said at least two sample chambers via diaphragms.

2. The sensor arrangement as claimed in claim 1, further comprising:
   a first module, which contains said at least two sample chambers.

3. The sensor arrangement as claimed in claim 2, further comprising:
   at least a second module, which has a plurality of potentiometric FET-sensors.

4. The sensor arrangement as claimed in claim 3, wherein:
   said electrolyte bridge extends via electrolyte canals which are integrated in said second module.

5. The sensor arrangement as claimed in claim 3, wherein:
   said reference cell has a potentiometric reference-FET-sensor for providing a pseudo-reference-potential, which is registered against the reference-potential of a reference electrode.

6. The sensor arrangement as claimed in claim 5, wherein:
   said reference electrode is contacted with the reference medium in said reference cell.

7. The sensor arrangement as claimed in claim 6, wherein:
   the potentials $U_{diff1}, U_{diff2}, \ldots U_{diffN}$ of N FET-sensors in the sample chambers are determined against the pseudo-reference-potential, and the measured-variable-relevant, potential differences are, in each case, determined by difference formation between the pertinent potential and the reference potential—thus, in the case of pH, according to the formulas $U_{pH1\ldots N} = U_{diff1\ldots N} - U_{diffref}$.

8. The sensor arrangement as claimed in claim 2, further comprising:
   a plurality of second modules, each of which has a potentiometric FET-sensor.

9. The sensor arrangement as claimed in claim 2, wherein:
   said first module comprises a plate-shaped platform with bores, which serve as sample chambers.

10. The sensor arrangement as claimed in claim 9, wherein:
    said bores traverse the platform; and
    said at least a second module, or second modules, are embodied as floor elements, which close the traversing bores from the underside of said first module.

11. The sensor arrangement as claimed in claim 9, wherein:
    said potentiometric FET-sensors are integrated into said second module in such a manner that, in each case, a FET-sensor aligns with its one of the traversing bores.

12. The sensor arrangement as claimed in claim 1, wherein:
    said electrolyte bridge extends via electrolyte canals, which are formed in the platform.

13. The sensor arrangement as claimed in claim 12, wherein:
    said platform comprises a plurality of elements, preferably a plurality of layers, and the electrolyte canals are located in an interface between two neighboring elements.

* * * * *